United States Patent [19]

Scott

[11] Patent Number: 5,045,461

[45] Date of Patent: Sep. 3, 1991

[54] METHOD FOR INCREASING YIELD AND NODULATION BY BRADYRHIZOBIUM

[75] Inventor: Kieran F. Scott, Waverly, Australia

[73] Assignee: Lubrizol Genetics, Inc., Wickliffe, Ohio

[21] Appl. No.: 213,906

[22] Filed: Jun. 30, 1988

[51] Int. Cl.[5] .................. C12N 15/09; C12N 1/21; C12N 1/11

[52] U.S. Cl. .................. 435/172.3; 435/252.2; 435/252.3; 435/320.1; 435/878; 536/27; 935/38; 935/64; 935/72

[58] Field of Search .................. 435/172.3, 317.1, 878, 435/252.2, 252.3, 320; 536/27; 935/29, 30, 38, 41, 56, 64, 72

[56] References Cited

U.S. PATENT DOCUMENTS 4,782,022 11/1988 Puhler et al. .................. 435/172.3
4,863,866 3/1987 Zablotowicz et al. .

OTHER PUBLICATIONS

Scott (1986) Nucleic Acids Research 14: 2905–2919.
Burn, et al. (1987), Genes and Development 1:456–464.
Nieuwkoop, et al., (1987) Journal of Bacteriology 169: 2631–2638.
Schofield and Watson (1986) Nucl. Acids Res. 14:2891–2903.
Nieuwkoop et al., (1987) J. Bact. 169:2631–2638.
Scott (1986) Nucl. Acids Res. 14:2905–2919.
Burn et al. (1987) Genes and Development 1:456–464.
Mazodier et al. (1985) Nucl. Acids. Res. 13:195–205.

Primary Examiner—Jacqueline Stone
Assistant Examiner—Che S. Chereskin
Attorney, Agent, or Firm—Greenlee and Associates

[57] ABSTRACT

A method of increasing nodulation of a plant capable of being nodulated by *Bradyrhizobium* sp. (*Parasponis*) is provided comprising infecting said plant with a *Bradyrhizobium* sp. (*Parasponia*) species mutated such that nodK is non-functional. One such method of mutation involves insertion upstream of nodABC constitutive promoter sequences capable of activating nodABC. The invention is exemplified by the inoculation of siratro with mutated *Bradyrhizobium* sp. (*Parasponia*) mutated by insertion of nptII promoter sequences in nodK upstream of nodABC so as to activate nodABC. As compared with inoculation with the corresponding wild-type *Bradyrhizobium* sp. (*Parasponia*), nodulation onset occurred five days earlier, nodulation number was doubled, and a 120% enhancement of plant yield was shown. Similar results were obtained regardless of the orientation of the nptII promoter-containing sequences within the nodK coding sequence.

10 Claims, 4 Drawing Sheets

FIG. IA
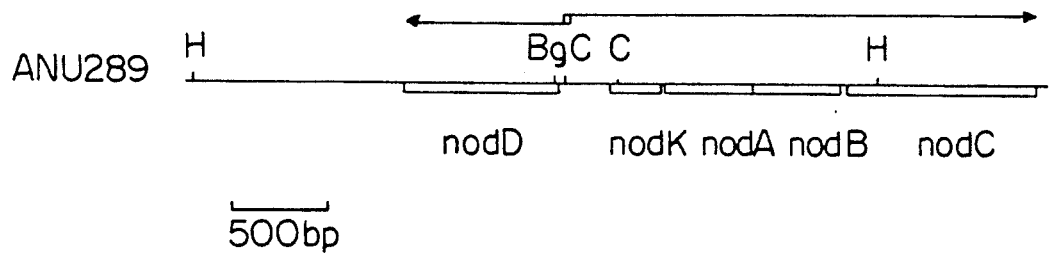
FIG. IB
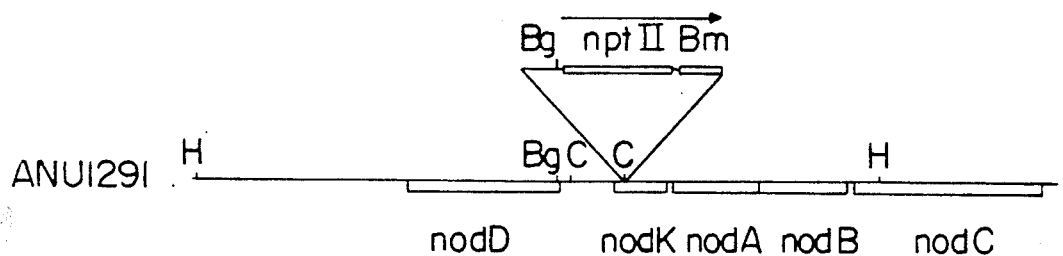
FIG. IC
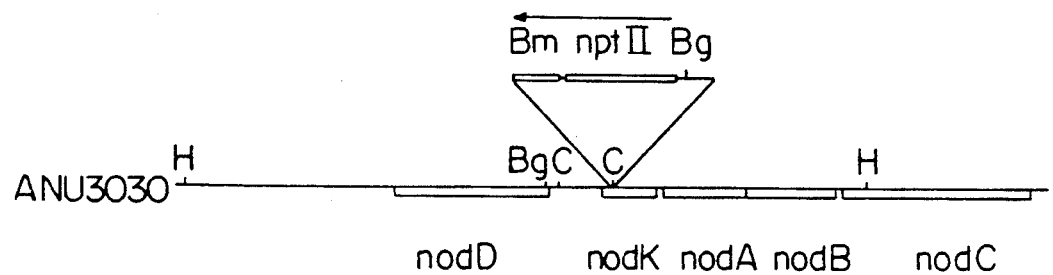

METHOD FOR INCREASING YIELD AND NODULATION BY BRADYRHIZOBIUM

FIELD OF THE INVENTION

This invention lies in the field of microbiology, and in particular discloses mutated Bradyrhizobium capable of increasing nodulation and yield in host plants.

BACKGROUND OF THE INVENTION

Soil bacteria of the genus Rhizobium, a member of the family Rhizobiaceae, are capable of infecting plants and inducing a highly differentiated structure, the root nodule, within which atmospheric nitrogen is reduced to ammonia by the bacteria. The host plant is most often of the family Leguminosa. Previously, Rhizobium species were informally classified in two groups, either as "fastgrowing" or "slow-growing" to reflect the relative growth rates in culture. The group of "slow-growing" rhizobia has recently been reclassified as a new genus, Bradyrhizobium (Jordan, D.C. (1982) Int. J. Syst. Bact. 32:136). The fast-growing rhizobia include *Rhizobium trifolii, R. meliloti, R. leguminosarum* and *R. phaseolus.* These strains generally display a narrow host range. Fast-growing *R. japonicum* which nodulate wild soybeans, *Glycine max* cv. Peking and siratro, and fast-growing members of the cowpea *Rhizobium* display broader host range. *R. japonicum* strains form only ineffective nodules on commercial soybean cultivars. The slow-growing rhizobia, now a distinct genus called Bradyrhizobium, include the commercially important soybean nodulating strains *Bradyrhizobium japonicum* (i.e., USDA 110 and USDA 123), the symbiotically promiscuous rhizobia of the "cowpea group," and *Bradyrhizobium* sp. *(Parasponia)* (formerly Parasponia Rhizobium) which nodulates the nonlegume *Parasponia,* as well as a number of tropical legumes including cowpea and siratro.

Nodulation and development of effective symbiosis is a complex process requiring both bacterial and plant genes. The symbiotic association between bacteria of the genus *Bradyrhizobium* or *Rhizobium* and leguminous plants results from a set of both temporally and spatially defined interactions between the plant host and the microorganism. These interactions are mediated through the expression of a number of bacterially-encoded and plant-encoded genes (Vincent, J.M. (1977) in Rhizobium General Microlrology. *A Treatise on Dinitrooen Fixation* Section III, R.W.F. Hardy and W.S. Silver (eds.), Wiley, N.Y., pp. 277-366). The temporal coordination of the early steps of nodule formation is achieved, at least in part, through the induction of bacterial nodulation gene expression by low molecular weight signal molecules from the host (Redmond et al. (1986) Nature 323:632-636; Peters *et al.* (1986) Science 223:977-979) and the reciprocal requirement for the expression of certain bacterial gene products prior to the induction of host gene expression (Govers *et al.* (1986) Nature 323:564-566).

Microscopy studies have shown that the infection process begins with attachment of bacteria to the root hair surface, induction of a root hair curling response and infection thread formation. This thread then grows down through the root hair cell into cortical tissue. For nodules with a determinate structure, cell division is induced in the pericycle and cortical tissue of the root at an early stage of infection. The infection thread continues to grow and ramifies within the expanding cortical zone. Bacteria bud off from the infection threads and form bacteroides surrounded by a plant-derived membrane, and nitrogen fixation occurs within these structures (Bauer, W.D. (1981) Ann. Rev. Plant Physiol. 32:407-449). Studies of the timing of nodule development using spot inoculation assays have shown that under these conditions, the first events of root hair curling and the induction of cell divisions within the cortex and pericycle of the root occur within 24-48 hours after inoculation with bacteria (Calvert et al. (1984) Can. J. Bot. 62:2375-2384; Ridge, R.W. and Rolfe, B.G. (1986) J. Plant Physiol. 122:121-137).

Several recent reviews of the genetics of the Rhizobium-legume interaction are found in Broughton, W.J., ed. (1982) Nitrogen Fixation, Volumes 2 and 3 (Clarendon Press, Oxford); Puhler, A. (ed.) (1983) Molecular Genetics of the Bacteria-Plant Interaction (Cornell University Publishers, Ithaca, N.Y.); Long, S.R. (1984) in Plant Microbe Interactions Volume 1, Kosuge, T. and Nester, E.W. (eds.), McMillan, N.Y., pp. 265-306; and Verma, D.P.S. and Long, S.L. (1983) International Review of Cytology (Suppl. 14), Jeon, K.W. (ed.), Academic Press, p. 211-245.

In the fast-growing species, the genes required for nodulation and nitrogen fixation are located on large Sym (symbiotic) plasmids. Although the process of recognition, infection and nodule development is complex, it appears that at least for the fast-growing rhizobia relatively few bacterial genes are directly involved and these are closely linked on the Sym plasmid. For example, a 14 kb fragment of the Rhizobium trifolii Svm plasmid is sufficient to confer clover-specific nodulation upon a Rhizobium strain cured of its Svm plasmid, as well as on an Aorobacterium strain which does not normally nodulate plants (Schofield et al. (1984) Plant Mol. Biol. 3:3-11). Nodulation and nitrogenase genes are localized on symbiotic plasmids in R. leguminosarum (Downie et al. (1983) Mol. Gen. Genet. 190:359-365) and in *R. meliloti* (Kondorosi *et al.* (1984) Mol. Gen. Genet. 193:445-452).

Fine structure genetic mapping has been used to locate individual nodulation genes in fast-growing rhizobia. Transposon mutagenesis, most often using the transposon Tn5, has identified about 10 nodulation genes associated with non-nodulation, delayed nodulation and altered host range phenotypes (Djordjevic et al. (1985) Mol. Gen. Genet. 200:263-271; Downie *et al.* (1985) Mol. Gen. Genet. 198:255-262; Kondorosi et al. (1984) Mol. Gen. Genet. 193:445-452; Innes et al. (1985) Mol. Gen. Genet. 201:426-432; Kondorosi *et al.* (1985) *Nitrooen Fixation Research Progress,* Evans *et al.* (eds.) Martinus Nijhoff, Dordrecht, Netherlands, pp. 73-78; Long et al. (1985) ibid., pp. 87-93; Downie et al. (1985) ibid. pp. 95-100; Rolfe et al. (1985) ibid., pp. 79-85; Schofield and Watson (1985) ibid., p. 125).

Three "common" Sym plasmid encoded nodulation genes have been identified in *R. meliloti* (Torok *et al.* (1984) Nucl. Acids Res. 12:9509-9524; Jacobs et al. (1985) J. Bacteriol. 162:469-476), *R. leguminosarum* (Rossen *et al.* (1984) Nucl. Acids Res. 12:9497-9508) and *R. trifolii* (Schofield and Watson (1986) Nucl. Acids Res. 14:2891-2903; Rolfe *et al.* (1985) *Nitrogen Fixation Research Prooress,* Evans *et al.* (eds.), Martinus Nijhoff, p. 79-85; Schofield and Watson, *ibid.,* p. 125; Schofield Ph.D. Thesis (1984) Australian National University, Canberra, Australia). These genes, designated nodA, B and C, are associated with the early stages of infection and nodulation and are functionally and structurally conserved among fast-growing rhizobia. In *R. meliloti, R. leguminosarum* and *R. trifdii,* the nodA, B and C genes are organized in a similar manner and are believed to be coordinately transcribed as a single genetic operon. Mutations in these genes fail to develop visible nodules (Nod-) and in some cases fail to induce root hair curling which is prerequisite for infection.

The DNA region adjacent to nodA (5'- from the start of *nodA*) in *R. meliloti* was also reported to be involved in early nodulation function (Torok *et al.* (1984)supra). The region adjacent to the *nodABC* operon in fast-growing rhizobia has now been shown to contain an open reading frame, now designated *nodD*. The location and sequence of *nodD* has been determined in *R. meliloti* (Eglehoff *et al.* (1985) DNA 4:241–248), *R. leguminosarum* (Sherman *et al.* (1986) EMBO J. 5:647–652; Downie *et al.* (1985) Mol. Gen. Genet. 198:255–262) and *R. trifolii* (Schofield and Watson (1985) supra and 1986; Rolfe *et al.* 1985; Schofield, 1984) supra. Mutations in *nodD* of *R. meliloti* have been shown to be functionally complemented by the *nodD* gene of *R. trifolii* (Fisher *et. al.* (1985) Appl. Environ. Microbiol. 49:1432–1435Comparison of the sequences of nodD genes in the fast-growing rhizobia confirm that there is significant sequence conservation. *R japanicum* USDA 191, a promiscuous, fast-growing rhizobium, is also found to contain two distinct nodD-like genes, nodD-$r_1$ and nodD-$r_2$ (EPO Publication No. 0211662, 1987) These *nodD*-like genes are about 70% homologous to each other and both display about the same homology to nodD genes of other fast-growing strains. The structural conservation of the nodD genes confirms that these genes function similarly in the different strains.

In contrast to the fast-growing rhizobia, no Sym plasmids have been associated with nodulation by the slowgrowing rhizobia, *B. japonicum* or *Bradyrhizobium* sp. (*Parasponia*). The nitrogenase and nodulation genes of these organisms are believed to be encoded on the chromosome. Marvel *et al.* (1984) in *Advances in Nitrogen Fixation Research*, Veeger and Newton (ed.) Nijhoff/Junk, the Hague, Netherlands; and (1985) Proc. Natl. Acad. Sci. 82:5841–5845, have shown that a strain of *Bradyrhizobium* sp. (*Parasponia*) contains genes associated with early nodulation, which can functionally complement mutations in R. melilati nod gene mutants and which hybridize to the *nodABC* genes of *R. meliloti*. The use of bacterial mutants has shown that the bacterial genes nodA, nodB and nodC, induced in response to plant factors, are essential for the production of a soluble factor(s) which act(s) to initiate root hair curling and pericycle cell divisions in Bradurhizobium sp. (*Parasponia*).

Russell *et al.* (1985) J. Bacteriol. 164:1301–1308 report the isolation of DNA regions encoding nodulation functions in strains of *B. japonicum*. The isolated DNA region was reported to show strong homology to nod regions of *R. meliloti* and *R. leguminosarum,* and to functionally complement a *Nod-* mutation in *R. fredii.* No sequence or transcript mapping of the cloned DNA was provided.

The precise biochemical role of the nod genes and their products in nodule development is unknown. Attempts to isolate nod gene mRNA and protein products from freeliving Rhizobium have been unsuccessful (Kondorosi et al. (1984). Protein products of nod genes have, however, been obtained by fusion of *nod* genes to strong *E. coli* promoters (Schmidt et al. (1984) EMBO J. 3:1705-1711; John, M. *et al.* (1985) EMBO J. 4:2425-2430) or in an *E. coli in vitro* transcription/translation system (Downie et al. (1985) Mol. Gen. Genet. 198:255–262). Schmidt et al. (1984) report the expression in E. coli minicells of several polypeptides encoded in the *R. meliloti* common nod region. Three polypeptides of 23, 28.5 and 44 kd, respectively, were mapped to the nod gene cluster. The 44 kd protein maps to a region of DNA strongly conserved among fast-growing rhizobia. John et al. (1985) supra identified the 44 kd protein as the product of the nodC gene. A fourth polypeptide product of 17.5 kd is mapped to the region of the nodD gene in *R. meliloti*. Downie et al. (1985) supra report the production of the presumptive nod gene products of *R. leguminosarum* by an *in vitro* translation/transcription system. Four polypeptides having molecular weights of 48, 45, 36 and 34 kd were reported to be the products of the nod genes. The 34 kd and 36 kd polypeptides are described as originating from a single gene and are reported to be the products of nodD.

Because establishment of nitrogen-fixing nodules is a multistage process involving coordinated morphological changes in both bacterium and plant, it is expected that the rhizobial nodulation genes are under precise regulatory control.

It has been suggested that an exchange of signals between plant and bacterium is requisite for mutual recognition and coordination of the steps of infection and nodulation development (Nutum, P.S. (1965) in *Ecology of Soil Borne Pathogens,* F.K. Baker and W.C. Snyder (eds.), University Of California press, Berkeley, pp. 231–247; Bauer, W.D. (1981) Ann. Rev. Plant Phys. 32:407–449: and Schmidt, E.E. (1979) Ann. Rev. Microbiol. 33:355–376). For example, root exudates have been linked to control of nodulation. Exudates have been reported to both stimulate (Thornton (1929) proc. Royal Soc. B 64:481; Valera and Alexander (1965) J. Bacteriol. 89:113–139; Peters and Alexander (1966) Soil Science 102:380–387) and inhibit (Turner (1955) Annals Botany 19:149–160; and Nutman (1953) Annals Botany 17:95–126) nodulation by rhizobia.

Although there are many sites at which root hair curling and cell division can be seen to initiate, only a small percentage of these sites produce functional nodules (Calvert et al. (1984) Can. J. Bot. 62:2375–2384). Nodule number is also influenced by factors of both bacterial and plant origin. For example, there are plant mutants which fail to repress nodulation as is normally seen in wild-type plants, resulting in a "super-nodulation" phenotype (Carroll et al. (1985) Proc. Natl. Acad. Sci. (USA) 82:4162-4166). Similarly, bacterial mutants which are capable of nodule induction but fail to fix nitrogen, induce greater numbers of nodules on plant roots than their parent wild-type strain (Scott *et al.* (1982) J. Mol. Appl. Genet. 1:315–326). Biochemical analysis of these plant mutants (Gresshoff and Delves (1986) in *Plant Gene Research Vol. III. A Genetic Approach to Plant Biochemistry.* A.B. Blonstein and P.T. King (eds), Springer-Verlag, Wein) together with split root experiments using a variety of bacterial strains (Kosslak R.M. and Bohlool, B.B. (1984) Plant Physiol. 75(1):125–130) has led to the suggestion that the bacterium, on invasion, produces a signal which results in the production of a systemic inhibitor in the plant shoot which acts to repress further nodulation in the susceptible root zone.

Recently, the chemical factors in legume exudates that are responsible for stimulation of nod gene expression in Rhizobia have been identified. EPO Publication No. 0245931, 1987 identified a structural related class of molecules, certain substituted flavones and flavanones as nod gene inducing factors. Individual purified molecules, either isolated from clover exudates or available from commercial sources, were found to induce nod gene expression. U.S. Pat. Application 035,516 filed Apr. 7, 1987, now abandoned discloses the use of chemical factors, i.e. flavonoids as inducers of nod genes of *Bradyrhizobium japonicum.* See also Kosslak, R.M. *et al.* (1987) Proc. Natl. Acad. Sci. USA 84:7428-7432 which reported daidzein and genistein as the major components in soybean root exudate responsible for inducing the nod genes in *B. japonicum.*

In *R. meliloti* and *R. leguminosarum,* nodD is reported to be necessary in addition to plant factors for expression of the nodABC genes (Downie et al. (1985) Mol. Gen. Genet. 198:255-262; Mulligan and Long, (1985)Proc. Natl Acad. Sci 82:6609-6613; Rossen et al. (1985) EMBO J. 4:3369-3373. More recently, Shearman et al. (1986) EMBO J. 5:647-652, have reported that nodD is also required, in addition to plant factors for induction of nodF. Similarly, in *R. trifolii,* the nodABC genes are unable to confer root hair curling that is prerequisite for nodulation in the absence of the nodD gene (Schofield, Ph.D. Thesis (1984) Australian National University, Canberra). These results indicate that the nodD regulates the expression of other nod genes. The mechanism by which nodD regulates the expression of other nod genes is not yet known, but may involve the initial interaction of nodD directly or indirectly with legume exudate factors followed by binding of a product of nodD to DNA sequences in the promoter regions of the legume exudate inducible nod genes. In slow-growing rhizobia as well, e.g. in *B. japonicum* and Bradyrhizobium. sp. (Parasoonia), nodD has a similar regulatory function. See Nieuwkoop et al. (1987) J. Bact. 169:2631-2638; Scott (1986) Nucl. Acids Res. 14:2904-2919; and U.S. Pat. Applications 875,296 and 061,848, filed June 11, 1989, now allowed.

A highly conserved nucleotide sequence has been described in the promoter regions of several legume exudate inducible *nod* genes. This sequence precedes the *R. trifolii* nodABC and nodFE genes and the *R. meliloti* nodABC genes (Schofield and Watson (1986) Nucl. Acids Res. 14:2891-2904). The sequence has also been identified in the promoter region of the nodABC genes in the slow-growing *Bradyrhizobium* sp. *(Parasponia)* Scott (1986) Nucl. Acids Res. 14:2905-2919). More recently, the rhizobial nod consensus sequence has been described as t'. . . ATCCAYNNYNNYGYR-GATGNWYKYKATCSAAWCAATCRATTTTAC-CARWYYKNSRR . . . 3'where N is A or G or C or T, Y is C or T, R is A or G, W is A or T, K is G or T and S is C or G. This sequence is believed to function in the regulation of expression of nod genes by chemical factors in legume exudate (Scott (1986) supra.

Scott (1986) supra describes and provides a a sequence for an open reading frame designated as nodK in Bradyrhizobium sp. (Parasponia) in the region between nodD and nodABC. This region is not present in fast-growing Rhizobia. Scott reports that computer analysis shows that nodK is as likely to be translated as nodA, nodB and nodC. Nieuwkoop et al. (1987) J. Bact. 169:2631-2638 report and provide a sequence for a similar open reading frame in R. japonicum having 30% homology to the Bradyrhizobium sp. (Parasponia) nodK.

While mutagenesis of host plants has yielded mutants with accelerated nodulation and increased nodule number, mutagenesis of bacteria has until now only yielded mutants which have altered host range, fail to nodulate, or are delayed in nodulation.

Burn, J. et al. (1987), "Four classes of mutations in the nodD gene of *Rhizobium leguminosarum* biovar *viciae* that affect its ability to autoregulate and/or activate other nod genes in the presence of flavonoid inducers," Genes and Development 1:456-464, report deficient ability to nodulate by *R. leguminosarum* in which nodABC were constitutively expressed.

Applicants know of no previous reports of the functionality of the nodK gene product, nor of the ability of insertions in this region, preferably insertions comprising constitutive promoters, to enhance nodulation and yield in host plants.

BRIEF DESCRIPTION OF THE DRAWINGS

FIG. 1 shows construction of mutants in the nodK open reading frame.

FIG. 1A: Restriction map of conserved nodulation gene region from parent strain ANU289.

FIG. 1B: and

FIG. 1C: Mutant constructs ANU1291 and ANU3030 respectively, showing the location of insertion of a 1.3 kb kanamycinresistance cassette in each case. Arrows indicate direction of transcription of known genes. Empty boxes show location of known nod gene coding regions. Shaded boxes indicate location of known coding regions on the mutagenesis cassette. H, HindIII; Bg, BolII; C, ClaI. Size markers are in kb.

SUMMARY OF THE INVENTION

Figure 2:
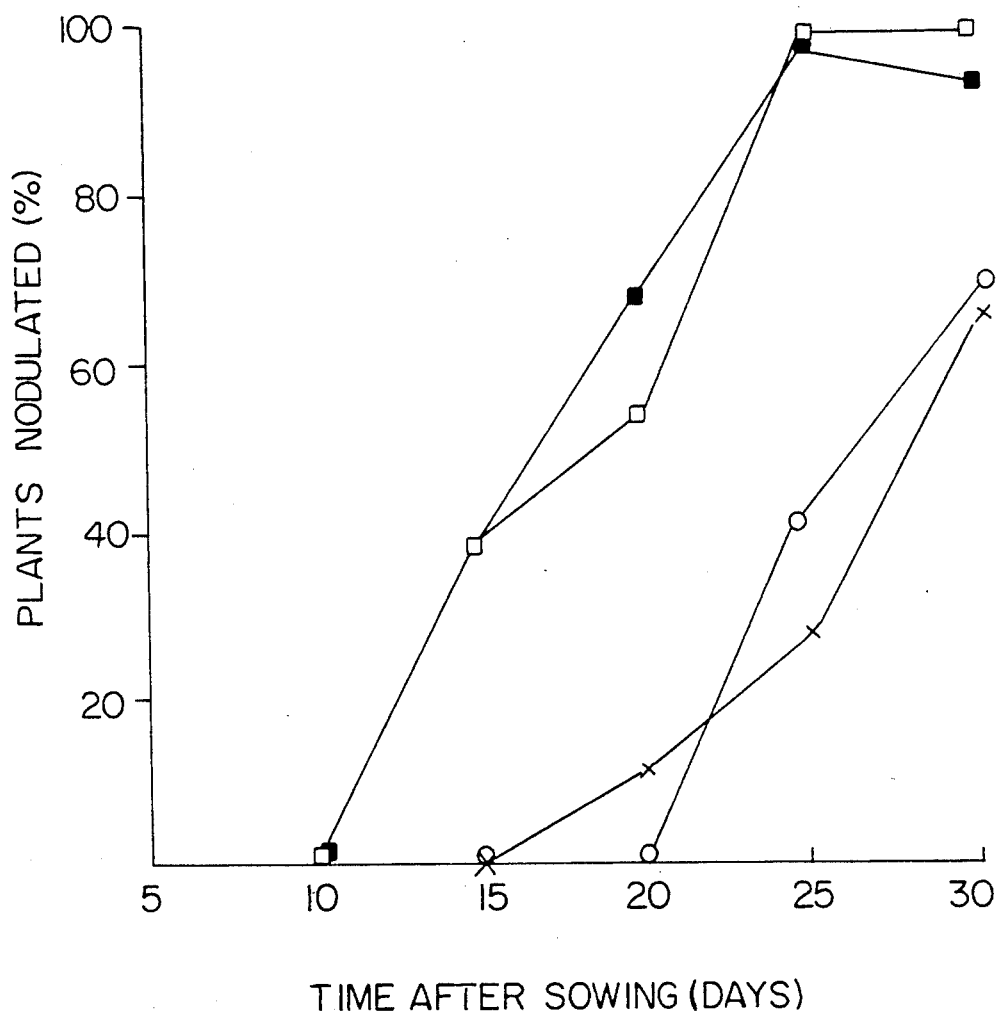
FIG. 2 shows timing of nodule induction in mutants. Siratro seeds were inoculated with the appropriate bacterial strain and allowed to grow. Replicate pots were harvested at each time point as described. The percentage of plants showing nodules is plotted against time after sowing. Each point is the average of two replicate trials each containing between seven and ten seedlings per pot. (x) Wild-type parent strain ANU289. (0) Wild-type inoculum strain Bradyrhizobium (sp. Cowpea) strain CB756. (□) Mutant strain ANU1291. (□) Mutant strain ANU3030. L.S.D. ($p < 0.05$) = 23.0

The often unstated aim of research into symbiotio nitrogen fixation is to genetically manipulate the symbiosis to enhance the yield of agriculturally important plants under nitrogen limiting conditions. The methods and organisms described herein enable the increase of nodulation and yield in host plants infected with the mutated Bradyrhizobium of this invention.

A method of enhancing nodulation of a plant capable of being nodulated by Bradyrhizobium sp. (Parasponia) is provided comprising infecting said plant with a strain of a Bradyrhizobium sp. (Parasponia) species mutated such that nodK is nonfunctional. Since nodK and nodABC are part of the same operon, it must also be ensured that transcription of nodABC is not disrupted by the mutation. Enhanced nodulation may involve increasing the number of nodules formed on the host plant over the number which would be formed with an unmutated strain of the same organism, or it may involve the production of nodules earlier than would be the case with the unmutated strain.

Methods of infecting a host plant with Bradyrhizobium strains are well-known to the art. It may be necessary to ensure the absence of unmutated *Bradyrhizobium* which will compete with the mutated species of this invention.

The term nodK as used herein refers to the first open reading frame upstream from nodABC labeled nodK in FIG. 1.

The complete sequence for some of the nodulation genes, including nodK of Bradyrhizobium sp. (Parasponia) is given in Scott, K.F. (1986), "Conserved nodulation genes from the nonlegume symbiont Bradyrhizobium sp. (Parasponia), Nucl. Acids Res. 14:2905-2919. The sequence of nodK in Bradyrhizobium sp. (Parasoonia) is as follows:

ATG GCG CGC CTG TTC ATC GCA GTT ATC GCA ATT CAA GGC GCG TCG

AAG ATG CAT AGA ACC GAA GTT GAT CTG GTG CCA GTC GGG TGT GTC

CTC GAT GAG CTC TCA CGC ATC GAT GGC CTG CCC CGC GAT GCG ACA

GCG CCG ATC TTG ATC TTG GAC GAG GCG GAG CCC CTT CAT GCT GCA

GAC AGG CTC CGG GCA ATC GGA TCG CTT CCT TGG GAC GTA CGC GCA

TGT TTC GGC CAT GGC ATT GGC CGG AAA GAT GCG CGC GAG ATG CGC

GAT CGT CTT GCC GCC AAC GAA GCC GCC ATT CCG ATT CGG TCT GCT

CTC GCG CGG TCT GCG AGG AGA GCC GAG CGC GGA TGC CGC ATG CCA

GCG CAT TTC AGA TTG ATC ACC GGT TCG GCA AAT AGC GAG TTT CTT

ACG TGA

Sequences having at least about 90% homology to the foregoing are considered equivalent thereto.

Techniques for inactivating genes by mutation are well-known to the art, as are techniques for ensuring that the mutation does not disrupt transcription of genes downstream in the same operon. Preferably the mutation is done by insertion mutation at a convenient restriction site within the gene, for example, the ClaI site of the gene in pPR289-10 described in Scott (1986) Nucleic Acids Res. 14:2905-2919. The sequences inserted may comprise promoter sequences capable of activating nodABC downstream therefrom, preferably constitutive promoter sequences. Such promoter sequences ensure that nodABC expression products are produced. Constitutive promoter sequences allow expression of nodABC gene products even in the absence of regulation by the nodD gene product and the appropriate plant exudate inducers of nodD. NotII promoter sequences are preferred for insertion into nodK, however, many other suitable constitutive promoter sequences are known to the art. The nodK gene is nonfunctional when translation thereof into the protein normally expressed is prevented, and as shown herein, nonfunctionality of nodK in Bradvrhizobium sp. (Parasoonia) is evidenced by increased nodulation ability.

A method of increasing nodulation of a plant capable of being nodulated by Bradvrhizobium sp. (Parasoonia) is also provided comprising infecting said plant with a Bradyrhizobium sp. (Parasoonia) strain mutated by insertion, upstream of nodABC, of constitutive promoter sequences capable of causing activation of nodABC. It is preferred, but not essential that such promoter sequences be inserted into the nodK gene, preferably as described above. It is not essential, however, that the insertion be in so long as it is upstream from nodABC and positioned such that it is able to cause activation of nodABC. Such activation may, as is known to the art, be mediated by a nodD expression product. Many constitutive promoter sequences are known to the art; nptII provides preferred promoter sequences.

A method is also provided for enhancing the nodulating ability of a Bradvrhizobium sp. (Parasoonia) strain comprising transforming said species with a vector comprising sequences capable of inactivating nodK. Vectors capable of insertion of extraneous material into a genome are known to the art as are methods for screening for the desired mutation. Preferably the vector comprises a mutated nodK gene containing an insertion of extraneous DNA sequences which inactivate the gene. The vector is preferably capable of causing homologous recombination in the host strain. A mutated Bradvrhizobium sp. (Parasoonia) may thereby be produced having the mutated nodK region carried by the vector. More preferably, the extraneous DNA sequences comprise functional promoter sequences capable of activating nodABC, and most preferably, such promoter sequences are constitutive promoter sequences.

A method is also provided for enhancing the nodulating ability of a Bradvrhizobium sp. (Parasoonia) strain comprising transforming said species with a vector comprising sequences capable of causing constitutive activation of nodABC. Suitable vectors are described above, however, it is not necessary that the promoter sequences be inserted in nodK so long as they are upstream of nodABC and capable of activating nodABC even in the absence of nodD activation.

A method is also provided for enhancing nodulation of a plant capable of being nodulated by a rhizobial strain comprising a nodK gene having the sequences of a Bradyrhizobium sp. (Parasoonia) nodK gene as set forth above, or a sequence having at least about 90% homology thereto, comprising inactivating said gene, preferably by insertion mutation, and more preferably by a mutation causing constitutive expression of nodABC.

The term recombinant DNA molecule is used herein to distinguish DNA molecules in which heterologous DNA sequences have been artificially cleaved from their natural source or ligated together by the techniques of genetic engineering, for example by in vitro use of restriction enzymes or ligation using DNA ligase.

The process of cloning a DNA fragment involves excision and isolation of the DNA fragment from its natural source, insertion of the DNA fragment into a recombinant vector and incorporation of the vector into a microorganism or cell where the vector and inserted DNA fragment are replicated during proliferation of the microorganism or cell. The term cloned DNA fragment or molecule is used to designate a DNA fragment or molecule produced by the process of cloning and copies (or clones) of the DNA fragment or molecule replicated therefrom.

Experiments show that the enhanced nodulation produced by the above methods may be accompanied by increased yield in the host plant.

DETAILED DESCRIPTION OF THE PREFERRED EMBODIMENTS

In a preferred embodiment, mutants of Bradyrhizobium sp. (Parasponia) strain ANU289 have been constructed by insertion mutagenesis which are able to induce nodules on the tropical forage legume Macrootileum atroouroureum at least five days prior to those induced by either the parental wild-type strain or a commercial inoculum strain CB756.

The mutants were constructed using a terminatorless kanamycin-resistance cassette, derived from the *E. coli* transposon Tn5, inserted into nodulation gene *nodK*. It is not necessary that the mutants be constructed by insertion mutation. Any method of inactivating nodK may be utilized so long as transcription of nodABC is not interfered with. Nor is it necessary that insertion mutations comprise kanamycin resistance genes and promoter sequences. Any insertion which disrupts the functioning of nodK will be appropriate, again so long as nodABC remain functional. It is preferred that the insertion comprises a marker gene for identification of mutated organisms, and/or a constitutive promoter sequence which will serve to activate nodABC downstream from the insertion.

It is not strictly necessary that the insertion of promoter sequences be in the nodK gene. Any position in which they serve to activate nodABC may be used.

The mutants constructed in the preferred embodiments showed a two-fold increase in the number of nodules generated per plant relative to the wild-type parent strain. Of particular interest is the observation that the mutations in the nodK open reading frame resulted in a 120 percent enhancement of plant yield as measured by shoot dry weight, in plants grown under nitrogen-free conditions as compared with those inoculated with the wild-type parent.

Mutagenesis may be done by means known to the art. In the preferred embodiment, after in vitro insertion, preferably of the terminatorless kanamycin resistance cassette cloned in a suitable plasmid, preferably pANU20 (see Table 1), into a suitable restriction site of the nodK gene, preferably the ClaI site, in a suitable plasmid containing same, preferably pPR289-10 (see Table 1), recombinants are screened by means known to the art. Preferably the insertion comprises an antibiotic resistance marker gene, and screening of resistant organisms is done by restriction endonuclease analysis.

TABLE 1

| Bacterial strains and plasmids. | | |
|---|---|---|
| | Relevant Characteristics | Source |
| Strains | | |
| *Escherichia coli* | | |
| RR1 | hsdS20, ara14, proA2, lacY1, galK2, rspL20, xyl-5, mtl-1, lambda⁻, supE44 | Bolivar et al. (1977) Gene 2:95–113. |
| SM10 | Km$^r$, F⁻, thi-1, thr-1, leuB6, lacY1, tonA21, supE44, recA⁻, lambda⁻ RP4-2 (Tc::Mu) | Simon et al. (1983) Biotechnol. 1:784–791. |
| Bradyrhizobium sp. (Parasponia) | | |
| ANU289 | Sm$^r$, Nod⁻, Fix⁻ | Scott et al. (1983a) DNA 2:141–148. |
| ANU1291 | Km$^r$, ANU289 nodK::nptII, forward orientation. | This work |
| ANU3030 | Km$^r$, ANU289 nodK::nptII, reverse orientation. | This work |
| Bradyrhizobium sp. (Cowpea) | | |
| CB756 | Nos⁻, Fix⁻ | Commercially available |
| Plasmids | | |
| pPR289-10 | Ap$^r$, Cm$^r$, 5.3 kb HindIII fragment carrying *B. parasponia* nodD and nodKABC genes cloned in pBR328. | Scott (1986) Nucl. Acids Res. 14:2905–2919. |
| pANU20 | Ap$^r$, Cm$^r$, Km$^r$, 1.3 kb HindIII-SmaI fragment containing nptII gene from Tn5 cloned into pBR328 by the addition of ClaI linkers. | Iismaa (1987) Ph. D. Thesis, Australian National University, Canberra, Australia |
| pSUP202 | Ap$^r$, Cm$^r$, Tc$^r$, oriT from RP4 | Simon et al. (1983) Biotechnol. 1:784–791. |

Means for moving selected DNA into Bradyrhizobium are known to the art. In the preferred embodiment, recombinants containing the cassette in each orientation are recloned into a mobilizable suicide vector, preferably pSUP202, preferably at the HindIII site. This mutated sequence is then homogenotized back into the wild-type strain desired to be mutated and presumptive mutants screened for double reciprocal crossover.

In the preferred embodiment, the suicide vector constructs are transformed into a suitable *E. coli* strain for replication, preferably SM10, and transformants used as donor strains in bacterial crosses with Bradyrhizboium sp. (Parasponia). Desired transconjugants are selected, preferably by means of antibiotic resistance linked with the mutated sequences desired to be transferred, and screened for the loss of the suicide vector sequences by colony hybridization using a labelled suicide-vector DNA probe. In the preferred embodiment using pSUP202, streptomycin resistant, kanamycin resistant transconjugants are purified and screened for the loss of the suicide vector sequences by colony hybridization using labelled pSUP202 DNA probe. Genomic DNA from isolates which fail to hybridize is cleaved with an appropriate endonuclease(s), preferably BalII, electrophoresed, blotted, and again probed with suicide vector sequences, appropriate DNA from the mutation, preferably the kanamycin resistant cassette, and from the original plasmid containing the nodK region, preferably pPR289-10, to verify that a double reciprocal crossover event in the nodK region has occurred. Isolates corresponding to mutants with an insertion mutation, preferably including a constitutive promoter in either orientation may be selected for inoculation of plants.

Host plants are inoculated with the mutated Bradyrhizobium to obtain nodulation earlier than with inoculation by the corresponding wild-type strain; nodulation number is increased and plant yield is increased. The following examples demonstrate the use of mutated Bradvrhizobium sp. (Parasponia) of this invention to inoculate siratro. Similar results are achieved using other Bradvrhizobium to inoculate their corresponding host plants.

EXAMPLE

Except as noted hereafter, standard techniques for cloning, DNA isolation, amplification and purification, for enzymatic reactions involving DNA ligase, DNA polymerase, restriction endonucleases and the like and various separation techniques are those known and commonly employed by those skilled in the art. A number of standard techniques ar described in: Maniatis et al. (1982) Molecular Cloning, Cold Spring Harbor Laboratory, Cold Spring Harbor, N.Y.; Wu (ed.) (1979) Methods Enzymol. 68: Wu et al. (eds.) (b 1983) Methods Enzymol. 100 and 101: Grossman and Moldave (eds.) 1980 Methods Enzymol. 65Miller (ed.) (1972) Experiments in Molecular Genetics, Cold Spring Harbor Laboratory, Cold Spring Harbor, N.Y.; Old and Primrose (1981) Principles of Gene Manipulation, University of California Press, Berkeley; Schleif and Wensink (1982) *Practical Methods in Molecular Biology:* Glover (ed.) (1985) *DNA Clonino* Vol. I and II, IRL Press, Oxford, UK; Hames and Higgins (eds.) (1985) *Nucleic Acid Hybridisation*, IRL Press, Oxford, UK; and Setlow and Hollaender (1979) *Genetic Engineering: Principles and Methods*, Vols. 114 4, Plenum Press, N.Y., which are incorporated by reference herein. Abbreviations, where employed, are those deemed standard in the field and commonly used in professional journals such as those cited herein.

Bacterial Strains and Plasmids. All bacterial strains and plasmids used in this work are listed in Table 1.

Media. LB, TY and TM media have been described (Miller, (1972,) supra Rolfe et al., 1980) Plant Sci. Lett. 19:211-284.

DNA Methods. Bacterial genomic DNA was isolated as described (Scott et al. (1983b) DNA 2:149-155). Large scale plasmid DNA isolation was as described by Humphreys et al. (1975) Biochim. Biophys. Acta 383:457-463, while rapid plasmid preparation was by the method of Holmes and Quigley (1981) Anal. Biochem. 114:193-197. Restriction endonucleases were obtained from Boehringer-Mannheim and New England Biolabs and used in accordance with the manufacturer's instructions. Isolation of DNA from agarose gels (Sea Plaque, Marine Colloids) was by electroelution. Transfer of DNA to nylon membrane (Amersham Hybond) was in accordance with the manufacturer's instructions. Hybridization conditions were as described by Reed and Mann (1985) Nucl. Acids Res. 13:7207-7221. DNA probes were prepared by random primed synthesis as previously described (Scott et a). (1983) DNA 2:149-155).

Bacterial Crosses. All matings were patch crosses as previously described (Scott et al. (1985) Mol. Gen. Genet. 201:43-50). Transconjugants were selected on solid TM medium containing streptomycin (200µg ml$^{-1}$) and kanamycin (600 µg ml$^{-1}$).

Plant Assay Procedures. Siratro seed was sterilized as described (Cen et al. (1982) Appl. Environ. Microbiol. 43:233-236), planted in a 1:1 vermiculite/perlite mix in 5 inch pots, inoculated with the appropriate bacterial strain (1 ml log phase culture per seed), covered with sterile plastic beads and grown in a solar glasshouse with 28° C. days and 10° C. nights. Plants were watered with nitrogenfree nutrient solution (Vincent (1970) A Manual for the Practical Study of Root Nodule Bacteria. IBP Handbook no. 15. Blackwell Scientific, Oxford) twice weekly until harvest. Shoot dry weight determinations were made after drying tissue at 80° C. for two days.

Nitrogen Fixation Assays. Nitrogenase activity was estimated by the acetylene reduction procedure as previously described (Scott et al. (1982) J. Mol. Appl. Genet. 1:315-326).

Construction of mutants in *nod*K. Mutations in the open reading frame designated nodK which precedes the nodABC operon in Bradyrhizobium sp. (Parasponia) strain ANU289 were made by the insertion of a terminatorless kanamycin resistance cassette, derived from Tn5 and cloned in pANU20 (Table 1), into the ClaI site of pPR289-10 located in the nodK gene (FIG. 1). pRPR289-10 is described in Scott, K.F. (1986) supra. Any source of nodK may be used in this invention; however. Any source for the kanamycin resistance gene may also be used with ClaI linkers added as is known to those skilled in the art. The cassette contains a functional notII gene and the first 51 codons of a bleomycin resistance gene immediately 3' to nptII (Mazodier et al. (1985) Nucl. Acids Res. 13:195-205). Kanamycin resistant recombinants were screened by restriction endonuclease analysis and constructs containing the cassette in each orientation were then recloned into the HindIII site of the mobilizable suicide vector pSUP202. This mutated sequence was then homogenotized back into the wild-type strain ANU289 and presumptive mutants screened for double reciprocal crossover as follows. The constructs were transformed into the *E. coli* strain SM10 and transformants used as donor strains in bacterial crosses with *Bradyrhizobium* sp. (Parasponia). Streptomycin resistant, kanamycin resistant transconjugants were purified and screened for the loss of pSUP202 sequences by colony hybridization using a labelled pSUP202 DNA probe. Genomic DNA was prepared from those isolates which failed to hybridize to the pSUP202 probe, cleaved with BalII, electrophoresed on an agarose gel, blotted and again probed with pSUP202 sequences, kanamycin resistance cassette sequences and pPR289-10 sequences to verify that a precise double reciprocal crossover in the nodK region had occurred. The pattern of hybridizing bands was consistent with the insertion of the 1.3 kb kanamycin resistance cassette into the ClaI site of nodK. Two isolates corresponding to mutants with the kanamycin resistance cassette in each orientation were identified and designated ANU1291 and ANU3030 respectively (FIG. 1).

Figure 3:
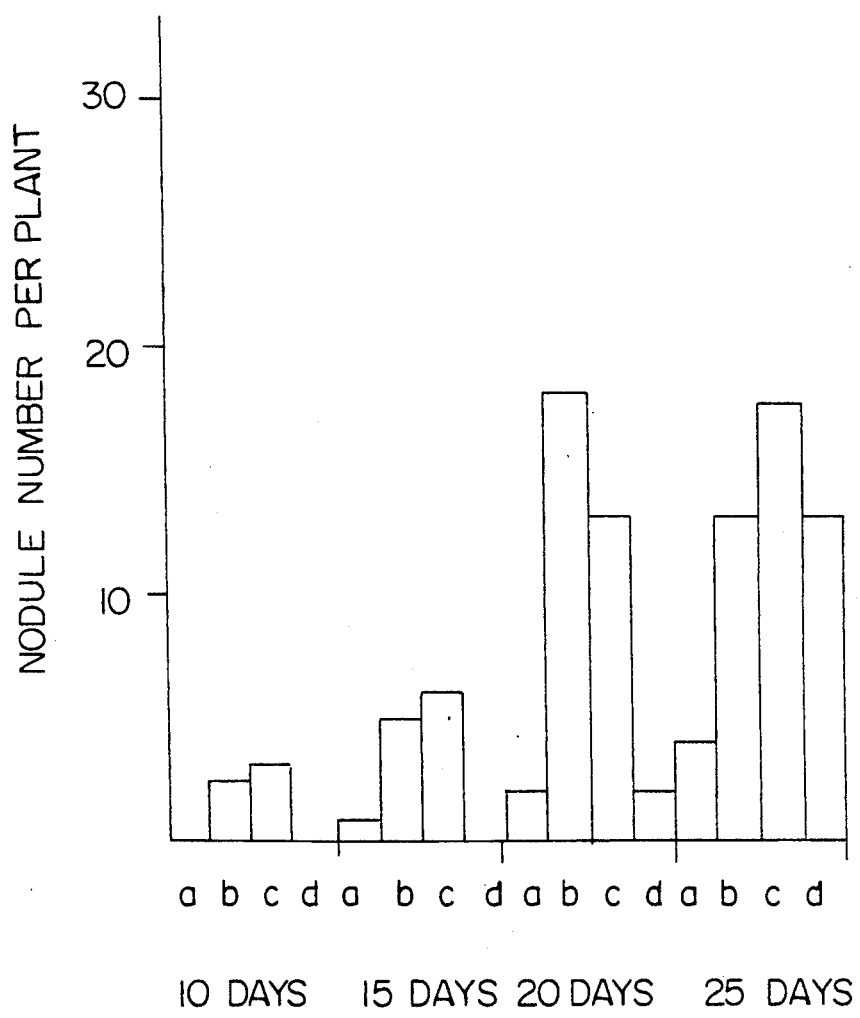
FIG. 3 shows a histogram of nodule number with time in mutants. Siratro seeds were inoculated with the appropriate bacterial strain and allowed to grow. Replicate pots were harvested at each time point and those plants containing nodules were analyzed for nodule number. Each bar is an average of the number of nodules per plant for each treatment. a) ANU289 b) ANU1291 c) ANU3030 d) CB756. L.S.D. ($p<0.05$) = 3.89

Nodulation Phenotype of nodK mutants on Macroptileum atropurpureum. To determine the phenotype of the nodK mutants on siratro, the two strains were screened first with the rapid plate assay procedure of Cen et al. (1982) Appl. Environ. Microbiol. 43:233–236. Both ANU1291 and ANU3030 produced nodules on siratro under these conditions (data not shown). Interestingly, the number of nodules formed appeared greater than those formed on inoculation with the wild type strain ANU289. In addition, nodulation appeared to occur earlier on those plants inoculated with the nodK mutants relative to ANU289. To quantify these observations a time course study of the nodulation properties of these strains was carried out in a duplicate pot assay. Ten siratro seeds were planted in 5 inch pots and inoculated with the appropriate Bradyrhizobium strain as described. Sufficient pots were set up to enable a duplicate harvest of each treatment at intervals of five days from 10–30 days after sowing. As shown in FIG. 2, the onset of nodulation for the two nodK mutant strains as measured by the percentage of plants containing nodules with time occurs at least five days prior to the onset of nodulation of both the parent strain ANU289 and a wild-type Bradyrhizobium (sp. cowpea) inoculum strain CB756. Acetylene reduction assays on nodulated plants from each time-point (data not shown) showed that the onset of nitrogen fixation was also advanced by at least five days relative to the two wild-type strains. Analysis of nodule number during this experiment (FIG. 3) confirmed the initial observation that the nodK mutants induced more nodules on siratro than ANU289. Inoculation with ANU1291 or ANU3030 resulted in, on average, twice the number of nodules relative to inoculation with ANU289.

Figure 4:
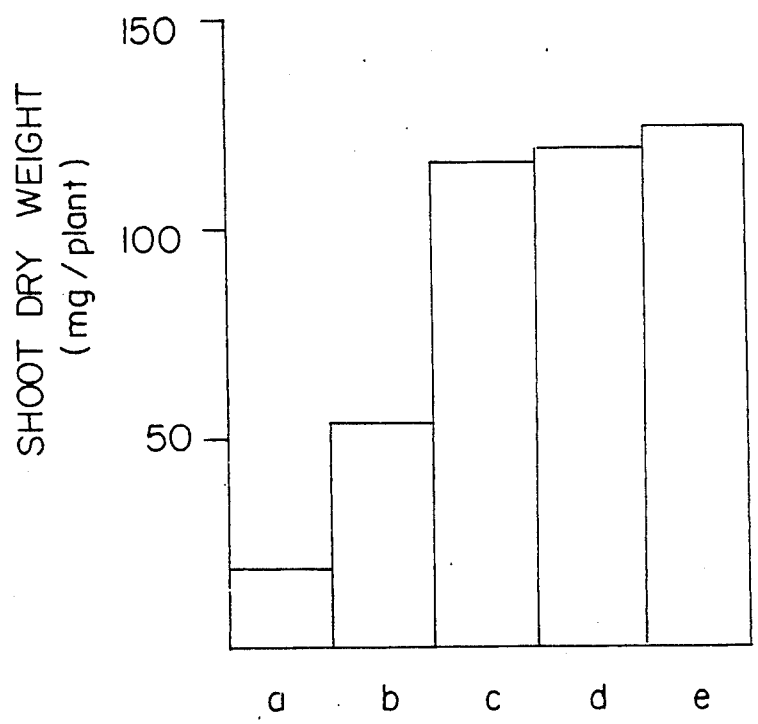
FIG. 4 shows yield of plants inoculated with mutant strains. Siratro seeds were inoculated with the appropriate bacterial strain, grown under conditions described for 60 days and harvested. Shoots were dried and weighed as described. Each bar represents an average of six replicates of each treatment, each containing between 15 and 20 plants per pot. a) Uninoculated control b) ANU289 c) ANU12941 d) ANU3030 e) CB756. L.S.D. ($p<0.05$) = 33

Effect of mutation in nodK on plant yield. To determine if the accelerated nodulation and nitrogen fixation phenotype observed on inoculation of siratro seed with the nodK mutants resulted in an enhancement of plant yield, a yield trial was conducted. Siratro seeds were sown in 5 inch pots (twenty per pot), inoculated with the appropriate bacterial strain and allowed to grow for sixty days as described in Materials and Methods. Six replicates of each treatment were set up and the yield results are shown in FIG. 4. The nodK mutants resulted in a 120% increase in yield as measured by shoot dry weight per plant relative to the parent strain ANU289. These data indicate that the accelerated nitrogen fixation and increased nodule number are not deleterious to plant growth under nitrogen limiting conditions but in fact serve to enhance it.

The aim of these studies was to investigate the symbiotic role of the open reading frame designated nodK and located 5' to nodABC in ANU289. Previous insertion mutations in the nodA gene immediately 3' to nodK resulted in complete loss of nodulation ability. Therefore, we decided to construct insertion mutations in nodK with a terminatorless kanamycin resistance cassette. In principle, this approach allows mutation of single genes in an operon by insertional inactivation without polar effects on the transcription of "downstream" genes in the operon since transcription would not be terminated by the insertion. The observation that mutants constructed in this way are able to nodulate siratro shows that the nodABC genes are expressed in the mutant strains regardless of the orientation of the kanamycin resistance gene. Therefore, the observed phenotype of the mutant strains is not due to the activity of the kanamycin gene.

The foregoing example is presented as illustrative rather than by way of limitation.

I claim:

1. A method of enhancing nodulation of a plant capable of being nodulated by Bradyrhizobium sp. (Parasponia) comprising:
   infecting said plant with a Bradyrhizobium sp. (Parasponia) strain mutated so that nodK is interrupted by an insertion, which insertion comprises promoter sequences capable of causing constitutive activation of nodABC.

2. The method of claim 1 in which said promoter sequences comprises nptII promoter sequences.

3. The method of claim 1 in which said plant is siratro.

4. A method for enhancing nodulation of a plant capable of being nodulated by a Bradyrhizobium sp. (Parasponia) strain comprising:
   infecting said plant with a Bradyrhizobium sp. (Parasponia) strain mutated by insertion upstream of nod ABC constitutive promoter sequences capable of activating nod ABC.

5. The method of claim 4 in which said promoter sequences comprise nptII promoter sequences.

6. The method of claim 5 in which said promoter sequences are inserted into nodK.

7. The method of claim 4 in which said plant is siratro.

8. A method for enhancing the nodulation ability of a Bradyrhizobium sp. (Parasponia) strain comprising:
   transforming said strain with a vector comprising promoter sequences capable of causing constitutive activation of nodABC.

9. A method of enhancing nodulation of a plant capable of being nodulated by a rhizobial strain comprising a nodK gene having the sequence:

```
ATG GCG CGC CTG TTC ATC GCA GTT ATC GCA ATT CAA GGC

GCG TCG AAG ATG CAT AGA ACC GAA GTT GAT CTG GTG CCA

GTC GGG TGT GTC CTC GAT GAG CTC TCA CGC ATC GAT GGC

CTG CCC CGC GAT GCG ACA GCG CCG ATC TTG ATC TTG GAC

GAG GCG GAG CCC CTT CAT GCT GCA GAC AGG CTC CGG GCA

ATC GGA TCG CTT CCT TGG GAC GTA CGC GCA TGT TTC GGC

CAT GGC ATT GGC CGG AAA GAT GCG CGC GAG ATG CGC GAT

CGT CTT GCC GCC AAC GAA GCC GCC ATT CCG ATT CGG TCT

GCT CTC GCG CGG TCT GCG AGG AGA GCC GAG CGC GGA TGC

CGC ATG CCA GCG CAT TTC AGA TTG ATC ACC GGT TCG GCA
```

AAT AGC GAG TTT CTT ACG TGA or a sequence having at least 90% homology thereto, said method comprising interrupting said gene with a DNA fragment comprising a promoter sequence such that nodABC are functional at a level sufficient for enhanced nodulation.

10. The method of claim 9 in which said plant is siratro.

* * * * *